United States Patent
Isomura et al.

(10) Patent No.: US 8,442,320 B2
(45) Date of Patent: May 14, 2013

(54) PATTERN INSPECTION APPARATUS AND PATTERN INSPECTION METHOD

(75) Inventors: Ikunao Isomura, Kanagawa (JP); Ryoichi Hirano, Tokyo (JP); Nobutaka Kikuiri, Tokyo (JP)

(73) Assignees: Kabushiki Kaisha Toshiba, Tokyo (JP); NEC Corporation, Tokyo (JP)

( * ) Notice: Subject to any disclaimer, the term of this patent is extended or adjusted under 35 U.S.C. 154(b) by 370 days.

(21) Appl. No.: 12/815,731

(22) Filed: Jun. 15, 2010

(65) Prior Publication Data

US 2011/0229009 A1 Sep. 22, 2011

(30) Foreign Application Priority Data

Mar. 17, 2010 (JP) ................................. 2010-060222

(51) Int. Cl.
*G06K 9/00* (2006.01)

(52) U.S. Cl.
USPC ........................................................ 382/181

(58) Field of Classification Search ................... 382/181, 382/229, 141, 153
See application file for complete search history.

(56) References Cited

U.S. PATENT DOCUMENTS

| 7,209,584 | B2 * | 4/2007 | Tsuchiya et al. | 382/145 |
|---|---|---|---|---|
| 7,630,535 | B2 | 12/2009 | Isomura | |
| 2004/0217288 | A1 * | 11/2004 | Sasajima et al. | 250/310 |
| 2006/0193508 | A1 * | 8/2006 | Sutani et al. | 382/145 |
| 2006/0245636 | A1 * | 11/2006 | Kitamura et al. | 382/149 |
| 2009/0097738 | A1 * | 4/2009 | Mamiya et al. | 382/150 |
| 2010/0067778 | A1 * | 3/2010 | Tamamushi | 382/145 |

FOREIGN PATENT DOCUMENTS

JP 2007-88375 4/2007

* cited by examiner

*Primary Examiner* — Edward Park
(74) *Attorney, Agent, or Firm* — Oblon, Spivak, McClelland, Maier & Neustadt, L.L.P.

(57) ABSTRACT

A pattern inspection apparatus includes: an optical image acquiring unit configured to acquire optical image data of a target object on which each of a plurality of identical patterns is respectively formed at a respective corresponding position of a plurality of forming positions with distortion; a cut-out unit configured to cut out a plurality of partial optical image data from the optical image data; a correction unit configured to correct positions of the plurality of partial optical image data by using distortion information from which each amount of distortion of the plurality of identical patterns respectively formed at the respective corresponding position of the plurality of forming positions on the target object can be acquired; and a comparison unit configured to compare a plurality of corrected partial optical image data against each other on a pixel to pixel basis.

10 Claims, 10 Drawing Sheets

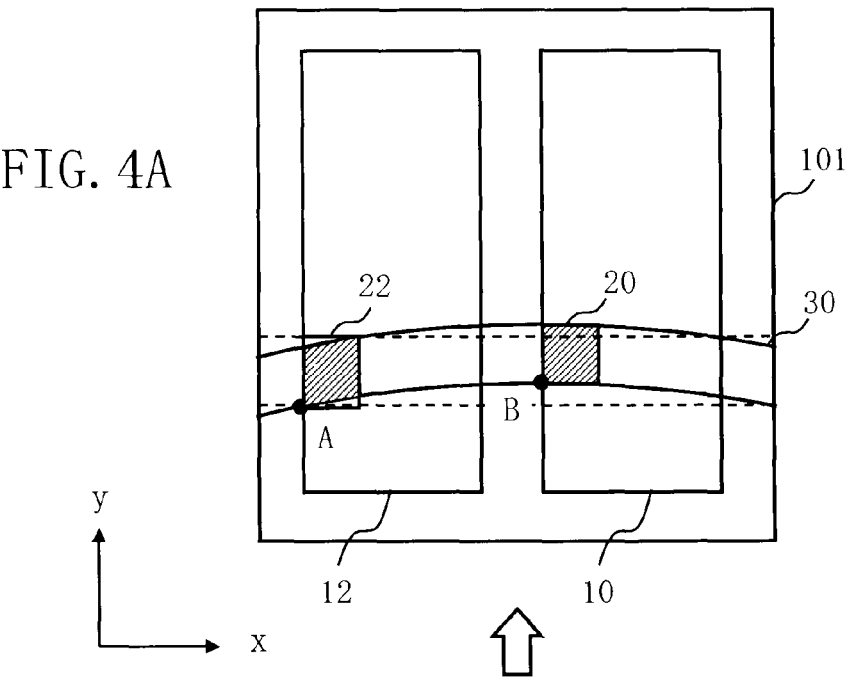
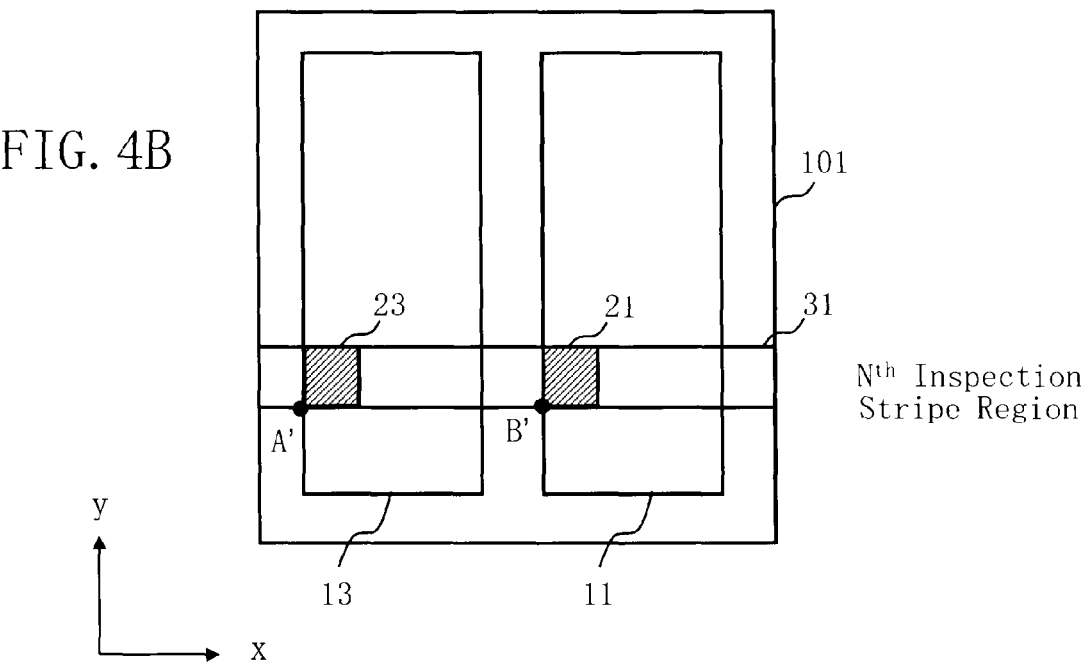

Correct Position

9 Points

PATTERN INSPECTION APPARATUS AND PATTERN INSPECTION METHOD

CROSS-REFERENCE TO RELATED APPLICATION

This application is based upon and claims the benefit of priority from prior Japanese Patent Application No. 2010-060222 filed on Mar. 17, 2010 in Japan, the entire contents of which are incorporated herein by reference.

BACKGROUND OF THE INVENTION

1. Field of the Invention

The present invention relates to a pattern inspection apparatus and a pattern inspection method, to a pattern inspection technique for inspecting a pattern defect of an object serving as a target used in, for example, semiconductor manufacturing, and to an apparatus which inspects a defect of an extremely small pattern of a photomask, a wafer, or a liquid crystal substrate used when a semiconductor element or a liquid crystal display (LCD) is manufactured and an inspection method therefor.

2. Related Art

In recent years, with increases in integration density and capacity of a large-scale integrated circuit, a circuit linewidth required for a semiconductor element becomes narrower. The semiconductor elements are manufactured by exposing a pattern to transfer the pattern onto a wafer by a reduced projection exposure apparatus so-called a stepper while using an original pattern (also called a mask or a reticle, to be generally called as a mask hereinafter) to form a circuit. Therefore, a pattern writing apparatus which can write a fine circuit pattern is used to manufacture a mask for transferring a fine circuit pattern onto a wafer. The pattern circuit may be directly written on a wafer by using the pattern writing apparatus. For example, the pattern is written by using an electron beam or a laser beam.

An increase in yield is necessary for manufacture of an LSI which requires huge manufacturing cost. However, as typified by a 1-Gigabit DRAM (Random Access Memory), a pattern configuring an LSI is now changing from an order of sub-micron meter to a nanometer. A pattern defect of a mask used when a super-fine pattern is exposed and transferred on a semiconductor wafer by a photolithography technique is one of great factors for reducing a yield. In recent years, with miniaturization of a size of an LSI pattern formed on a semiconductor wafer, a size which must be detected as a pattern defect is also very small. For this reason, a pattern inspection apparatus which inspects a defect of a transfer mask used in manufacture of an LSI is required to be precise.

On the other hand, with the advance of multimedia, in an LCD (Liquid Crystal Display), a liquid crystal substrate size is increased to 500 mm×600 mm or more, and miniaturization of a pattern for a TFT (Thin Film Transistor) or the like formed on a liquid crystal substrate is advanced. Therefore, a very small pattern defect in wide area is required to be inspected. For this reason, a pattern inspection apparatus which efficiently inspects a defect of a photomask used in manufacture of a pattern for the large-area LCD and a large-area LCD within a short period of time has been urgently needed.

For example, as a pattern inspection method, a "die to die inspection method in which optical image data obtained by imaging an identical pattern at different places on the same mask are compared with each other and a "die to database inspection" method in which image data (design image data) serving as a comparative reference is generated based on writing data (design pattern data) obtained by converting CAD data used when a mask pattern is written into an inspection apparatus input format and the image data is compared with measurement data (optical image data) obtained by imaging a pattern are known. In the inspection methods in the inspection apparatus, a target object is placed on a stage, and a beam scans the target object by moving the stage, thereby performing inspection. A beam is irradiated on the target object from a light source and an illumination optical system. A light transmitted through or reflected by the target object is focused on a sensor through the optical system. An image captured by the sensor is sent to a comparing circuit as optical image (measurement image) data. In the comparing circuit, after the images are aligned to each other, reference image data is compared with the optical image data according to an appropriate algorithm. When these data do not match with each other, it is determined that a pattern defect is present.

In this case, it has been primarily assumed that the pattern formed on the mask is transferred onto a semiconductor wafer or the like at its position on the mask when the pattern is transferred onto the semiconductor wafer or the like by an exposure apparatus. However, when a pattern is transferred by the exposure apparatus, a pattern shape or the like may be distorted by the optical system of the exposure apparatus, so that a patterned misaligned from the pattern formed on the mask is transferred onto the semiconductor wafer or the like. In order to utilize this fact, a technique, in which a pattern formed on a mask it self is distorted in advance such that the transferred pattern is at an ideal position according to transfer conditions of the exposure apparatus is developed.

When the mask on which a pattern is formed at a position distorted in advance as described above is inspected, the following problem occurs. In the die-die inspection, first, a mask is virtually divided into a plurality of inspection stripe regions of a strip shape, and image acquisition is performed for each of the inspection stripe regions. For one inspection stripe image, dies on which the identical pattern is formed exist to be compared with each other. The corresponding dies are cut out and compared with each other (for example, see Japanese Patent Laying-Open No. 2007-088375). In the die-die inspection, it is assumed that reference Y coordinates of the dies laterally arranged are equal to each other.

However, when a mask on which the distorted pattern is formed is inspected, positions (Y coordinates) of the corresponding patterns vary in an inspection stripe. For this reason, the positions of the dies to be compared with each other do not match with each other. For this reason, disadvantageously, accurate inspection cannot be executed.

As described above, when the die-die inspection is performed on a target object to be inspected on which a pattern distorted in advance is formed, the positions (Y coordinates) of the patterns of the corresponding dies vary. For this reason, the positions of the dies to be compared with each other do not match with each other. For this reason, disadvantageously, accurate inspection cannot be executed. In the past, a method that sufficiently solves the problem has not been established.

BRIEF SUMMARY OF THE INVENTION

In accordance with one aspect of this invention, a pattern inspection apparatus includes: an optical image acquiring unit configured to acquire optical image data of a target object on which each of a plurality of identical patterns is respectively formed at a respective corresponding position of a plurality of forming positions with distortion; a cut-out unit configured to cut out a plurality of partial optical image data from the optical image data; a correction unit configured to correct positions of the plurality of partial optical image data by using distortion information from which each amount of distortion of the plurality of identical patterns respectively formed at the respective corresponding position of the plurality of forming positions on the target object can be acquired; and a comparison unit configured to compare a plurality of corrected partial optical image data against each other on a pixel to pixel basis.

In accordance with another aspect of the invention, a pattern inspection method comprising: acquiring optical image data of a target object on which each of a plurality of identical patterns is formed at a respective corresponding position of a plurality of forming positions with distortion; cutting out a plurality of partial optical image data from the optical image data; correcting positions of the plurality of partial optical image data by using distortion information from which each amount of distortion of the plurality of identical patterns respectively formed at the respective corresponding position of the plurality of forming positions on the target object can be acquired; and comparing a plurality of corrected partial optical image data against each other on a pixel to pixel basis, to output a result of the comparing.

BRIEF DESCRIPTION OF THE DRAWINGS

FIGS. 4A and 4B are conceptual diagrams showing an example of dies in die-die inspection for an undistorted pattern and a distorted pattern according to Embodiment 1.

DETAILED DESCRIPTION OF THE INVENTION

Embodiment 1

In Embodiment 1, a pattern inspection apparatus which can perform accurate inspection when a die-die inspection is performed on a target object to be inspected on which a pattern distorted in advance is formed and a pattern inspection method will be described below.

Figure 1:
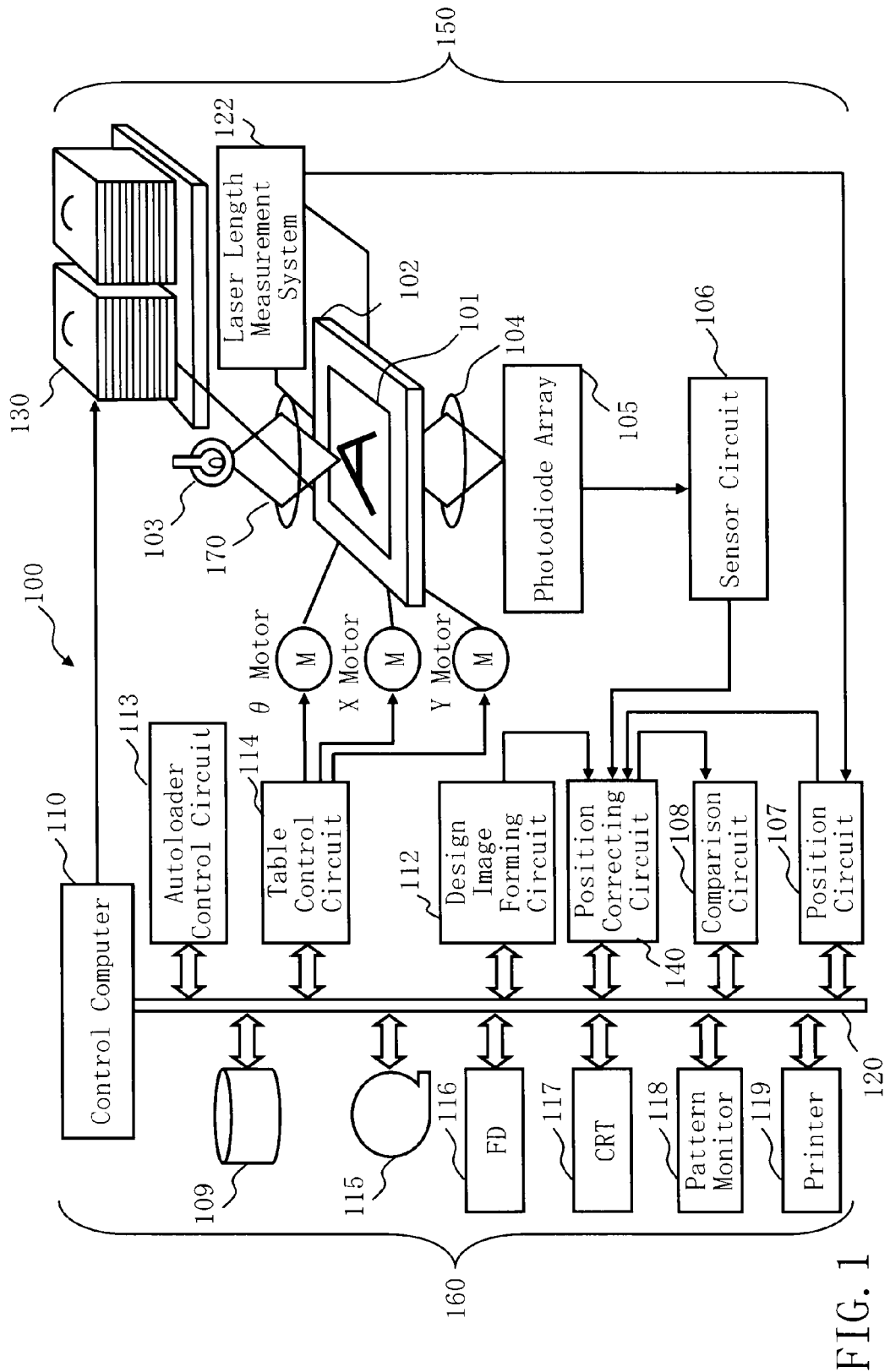
FIG. 1 is a conceptual diagram showing a configuration of a pattern inspection apparatus according to Embodiment 1.

FIG. 1 is a conceptual diagram showing a configuration of the pattern inspection apparatus according to Embodiment 1. In FIG. 1, a pattern inspection apparatus 100 which inspects a defect of a target object which is a substrate such as a mask includes an optical image acquiring unit 150 and a control circuit 160. The optical image acquiring unit 150 includes an XYθ table 102, an optical source 103, a magnifying optical system 104, a photodiode array 105, a sensor circuit 106, a laser length measurement system 122, an autoloader 130, and an illumination optical system 170. In the control circuit 160, a control computer 110 which is a computer is connected to a position circuit 107, a comparison circuit 108 which is an example of a comparison unit, a design image forming circuit 112, an autoloader control circuit 113, a table control circuit 114, a position correcting circuit 140, a magnetic disk apparatus 109 which is an example of a storage apparatus, a magnetic tape apparatus 115, a flexible disk apparatus (FD) 116, a CRT 117, a pattern monitor 118, and a printer 119 through a bus 120 which is a data transmission path. The XYθ table 102 is driven by an X-axis motor, a Y-axis motor, a θ-axis motor. In FIG. 1, a constituent portion required for explaining Embodiment 1 is described. The pattern inspection apparatus 100, in general, may include another necessary configuration as a matter of course.

Before the inspection is started, the autoloader 130 controlled by the autoloader control circuit 113 loads a photomask 101 which is a target object to be inspected on which a pattern is formed on the XYθ table 102 which is arranged to be moved by the X-axis, Y-axis, and θ-axis motors in a horizontal direction and a rotating direction and places the photomask 101 on the XYθ table 102. Information (design pattern data) of a design pattern used in pattern formation of the photomask 101 is input from an outside of the apparatus into the pattern inspection apparatus 100 and stored in the magnetic disk apparatus 109 which is an example of the storage apparatus (storage unit). In Embodiment 1, the design pattern data is an example of distortion information. Alternatively, the data is base data to provide distortion information.

The XYθ table 102 is driven by the table control circuit 114 under the control of the control computer 110. The XYθ table 102 can be moved by a drive system such as a 3-axis (X-Y-θ) motor which drives the table in the X direction, the Y direction, and the θ direction. As the X motor, the Y motor, and the θ motor, for example, step motors can be used. A moving position of the XYθ table 102 is measured by the laser length measurement system 122 and supplied to the position circuit 107. The photomask 101 on the XYθ table 102 is automatically conveyed by the autoloader 130 driven by the autoloader control circuit 113 and automatically discharged after the inspection is finished. The magnifying optical system 104 is driven by a piezoelectric conversion element or the like, and the image is focused on the photodiode array 105.

Figure 2:
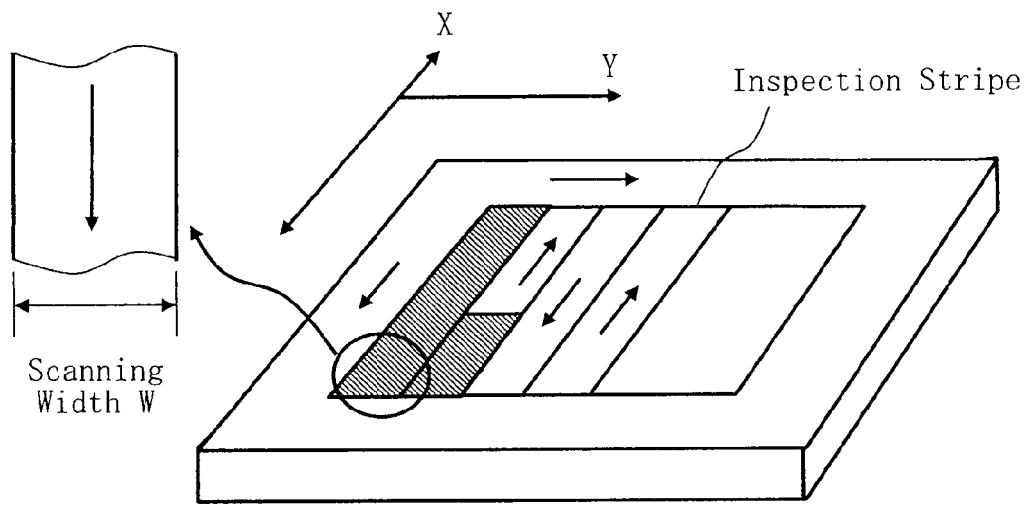
FIG. 2 is a diagram for explaining an acquiring procedure for an optical image according to Embodiment 1.

FIG. 2 is a diagram for explaining an acquiring procedure for an optical image according to Embodiment 1. A region to be inspected, as shown in FIG. 2, is virtually divided into a plurality of strip-shaped inspection stripes each having a scanning width Win, for example, the Y direction. The operation of the XYθ table 102 is controlled such that the divided inspection stripes are scanned continuously, and an optical image is acquired while the XYθ table 102 moves in the x direction. In the photodiode array 105, images each having the scanning width W as shown in FIG. 2 are continuously input. After an image of a first inspection stripe is acquired, an image of a second inspection stripe having the scanning width W is also continuously input while the table 102 is moved in the reverse direction in term. When an image on a third inspection stripe is to be acquired, the image is acquired while the table 102 is moved in a reverse direction of the direction in which the image of the second inspection stripe is acquired, i.e., in the direction in which the image on the first inspection stripe is acquired. In this manner, the images are continuously acquired to make it possible to shorten an unnecessary processing time. Although a forward (FWD)-backward (BWD) method is used here, an available method is not limited to the method and a forward (FWD)-forward (FWD) method may be used.

A light is irradiated on the pattern formed on the photomask 101 by the appropriate light source 103 arranged above the XYθ table 102. A beam irradiated from the light source 103 is irradiated on the photomask 101 through the illumination optical system 170. The light transmitted through the photomask 101 by illumination forms an optical image on the photodiode array 105 through the magnifying optical system 104 and is incident. The image of the pattern formed on the photodiode array 105 is photoelectrically converted by the photodiode array 105 and further A/D (analog-digital)-converted by the sensor circuit 106. On the photodiode array 105, sensors, for example, TDI (time delay integrator) sensors are arranged. In this manner, the optical image acquiring unit 150 acquires optical image data (stripe data) of the inspection stripes of the target objects to be inspected on which an identical pattern is arranged at a plurality of forming positions with distortion.

Measurement data (optical image data) of the inspection stripes output from the sensor circuit 106 are sequentially output to the position correcting circuit 140 every inspection stripe together with data output from the position circuit 107 and indicates a position of the photomask 101 on the XYθ table 102. The measurement data is, for example, 8-bit signless data for each pixel and expresses brightness gradients of the pixels in numbers, for example, 0 to 255. The light source 103, the illumination optical system 170, the magnifying optical system 104, the photodiode array 105, and the sensor circuit 106 configure a high-power inspection optical system.

Figure 3:
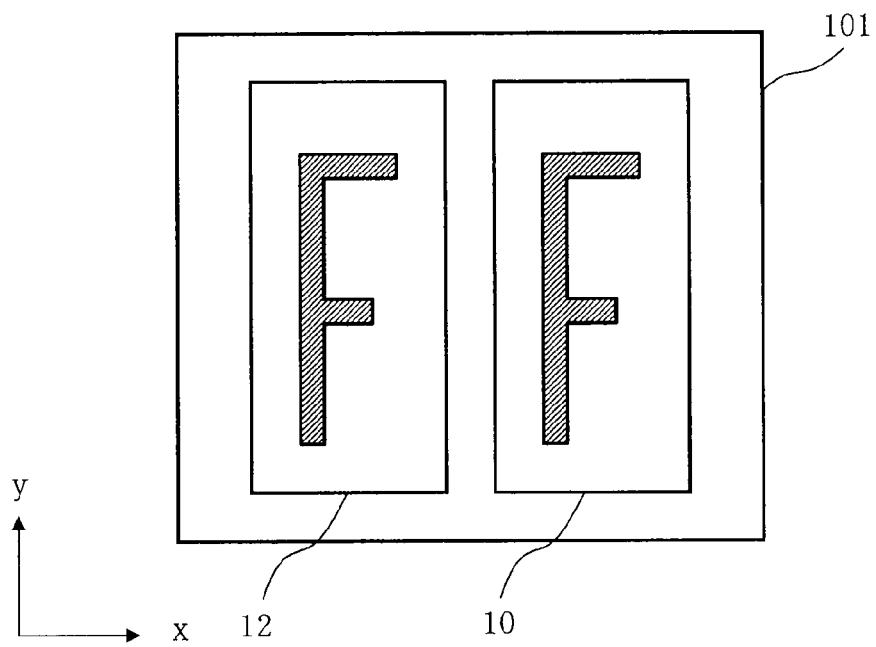
FIG. 3 is a conceptual diagram showing an example of a photomask and a formed pattern according to Embodiment 1.

FIG. 3 is a conceptual diagram showing an example of a photomask and a formed pattern according to Embodiment 1. In FIG. 3, on the photomask 101, a plurality of pattern regions 10 and 12 (regions to be inspected) written with an identical design pattern are formed. An entire region obtained by integrating the two pattern regions 10 and 12 is virtually divided into the plurality of inspection stripes shown in FIG. 2. Then, the optical image acquiring unit 150 acquires optical image data (measurement data) for each inspection stripe. For this reason, the measurement data of one inspection stripe includes both the images of the pattern regions 10 and 12.

FIGS. 4A and 4B are conceptual diagrams showing an example of dies in die-die inspection for an undistorted pattern and a distorted pattern according to Embodiment 1. It has been primarily assumed that a design pattern of a photomask is directly transferred onto a wafer or the like. However, in recent years, with narrowing of a linewidth of the design data, a pattern such as a fine pattern for optical proximity correction (OPC) which is not expected to be directly transferred onto a wafer or the like is frequently used. Furthermore, recently a technique which manufactures a pattern formed on a photomask by entirely distorting the pattern to satisfy transfer conditions of the exposure apparatus is developed. In Embodiment 1, the die-die inspection is performed on the photomask 101 on which the distorted pattern is formed. When the die-die inspection is to be performed on a conventional undistorted pattern, as shown in FIG. 4B, measurement data of one inspection stripe 31 includes partial optical images 21 and 23 which are dies to be compared between the pattern regions 11 and 13 on the same y coordinate. More specifically, a reference position B' of the partial optical image 21 and a reference position A' of the partial optical image 23 have different x coordinates and the same y coordinate. Therefore, when measurement data (optical image data) of each inspection stripe is divided with a predetermined width in an x direction and relatively moved in the x direction, the partial optical images 21 and 23 can be aligned.

However, an object to be inspected in Embodiment 1 is a target object to be inspected on which each of a plurality of identical patterns is respectively formed at a respective corresponding position of a plurality of forming positions with distortion. In a distorted pattern to be inspected in Embodiment 1, since a pattern position is originally distorted, an ideal inspection stripe 30 is also distorted. For example, as shown in FIG. 4A, a long side is transformed from a straight line to a moderate curve. For this reason, the partial optical images 20 and 22 which are dies to be compared between the pattern regions 10 and 12 have different x coordinates and different y coordinates. In actual image acquisition, an image is not acquired in a trace like the ideal distorted inspection stripe 30 as shown in FIG. 4A. The image is acquired, for example, in a rectangular (oblong) inspection stripe having straight long sides as shown in FIG. 4B. For this reason, even though the partial optical images 20 and 22 which are dies to be compared between the pattern regions 10 and 12 are caused to directly overlap, the image positions do not match. In inspection performed in this state, the pattern is determined as a defect.

Therefore, in Embodiment 1, the positions of the partial optical images 20 and 22 which are dies compared between the pattern regions 10 and 12 are corrected by using distortion information. In Embodiment 1, as the distortion information, writing data (design pattern data) obtained by converting CAD data used when the distorted pattern is written on the photomask 101 into an inspection apparatus input format is used. A conventional inspection apparatus which compares measurement data with design data generated by a design pattern used when the measurement data is provided is present. However, the apparatus is to directly compare both the data with each other, and is not different from an information input to change positions of the objects to be compared as in Embodiment 1.

First, the design image forming circuit 112 shown in FIG. 1 reads design pattern data from the magnetic disk apparatus 109 through the control computer 110 for each predetermined region. The read design pattern data of the photomask 101 is converted (developing process) into design image data which is binary or multi-valued image data. The predetermined regions may be regions (areas) of images corresponding partial optical images of dies to be compared.

Figure 5:
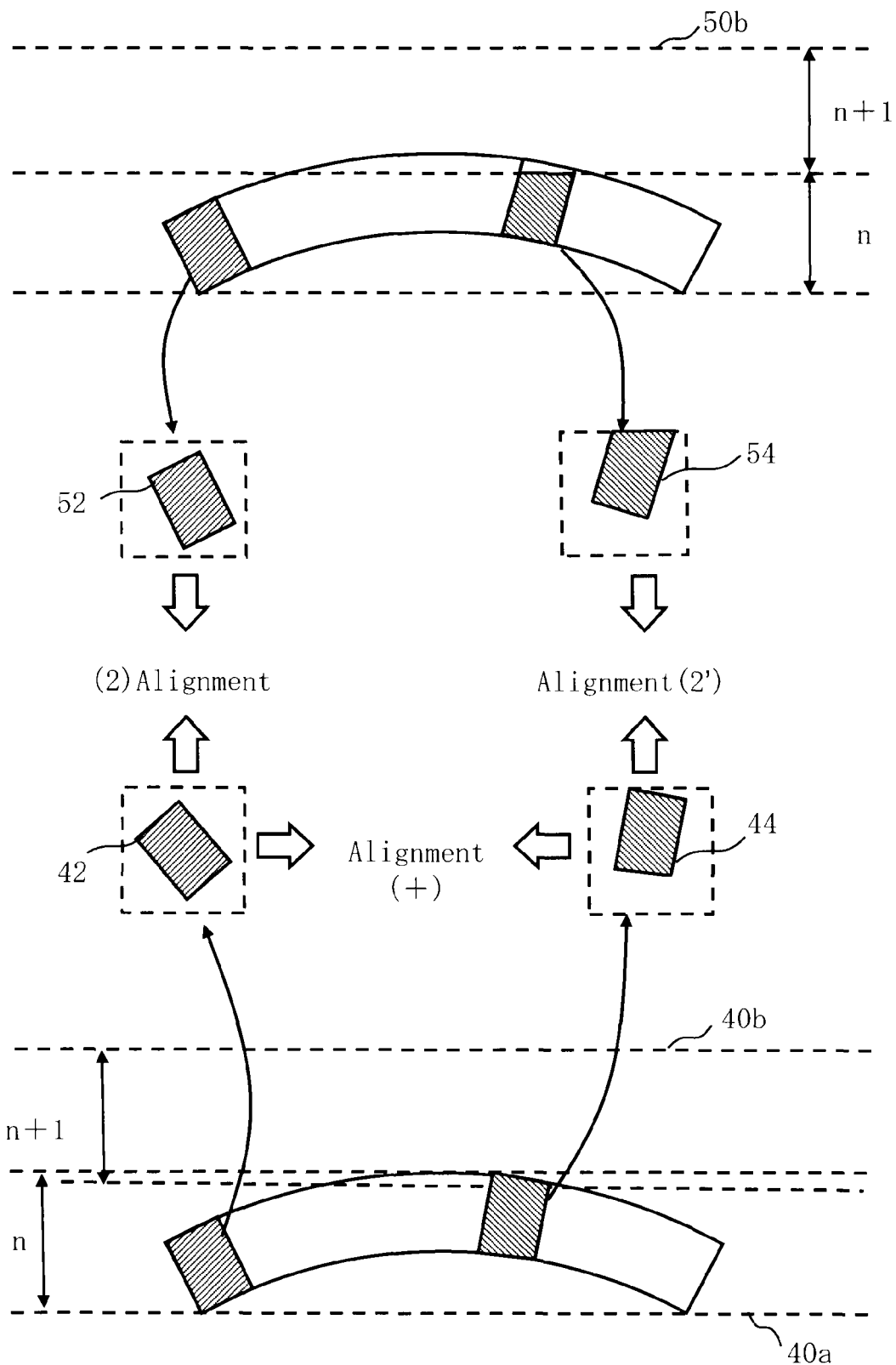
FIG. 5 is a conceptual diagram for explaining a method of correcting a position according to Embodiment 1.

FIG. 5 is a conceptual diagram for explaining a method of correcting a position according to Embodiment 1. For example, as shown in FIG. 5, all partial optical images of dies that would have been compared if a pattern were formed without distortion in optical image data (stripe data) may not fit into an $n^{th}$ inspection stripe 50a acquired from the photomask 101. For this reason, an overextended portion is inspected by using optical image data acquired on a $(n+1)^{th}$ inspection stripe 50b. However, in formation of design image data, the design image data is formed based on an $n^{th}$ inspection stripe 40a having a width including the overextended portion of the optical image data. In Embodiment 1, a design image is not used in comparison with a measurement image in inspection, but is used for positional correction between partial optical images 52 and 54 of dies to be compared. For this reason, the design image data is preferably formed such that the regions corresponding to all the partial optical images 52 and 54 of the dies to be compared are included in the stripe. In this manner, a lacking portion can be eliminated, and partial design images 42 and 44 corresponding to the partial optical images 52 and 54 (will be described later) can be easily aligned. The $(n+1)^{th}$ inspection stripe 40b used for formation of design image data on the assumption that the $(n+1)^{th}$ inspection stripe 40b overlaps the $n^{th}$ inspection stripe 40a to completely include the region of the $(n+1)^{th}$ inspection stripe 50b for optical image data. In this manner, also in die-die inspection for the optical image data acquired on the $(n+1)^{th}$ inspection stripe 50b, corresponding partial design image can be acquired.

A graphic constituting a pattern defined for design pattern data includes a rectangle or a triangle as a basic graphic. In the design pattern data, graphic data which defines shapes, sizes, positions, and the like of pattern graphics by information, for example, coordinates (x, y) at a reference position of a graphic, a length of a side, and a graphic code which is an identifier which identifies a graphic type such as a rectangle or a triangle is stored.

When the graphic data is input to the design image forming circuit 112, the graphic data is developed into data of the graphics, and a graphic code, a graphic size, and the like indicating graphic shapes of the graphic data are interpreted. As a pattern arranged in a grid which is a unit grid having a predetermined quantization size, binary or multi-valued image data is developed. The image data which is developed (developed image data) is stored in a pattern memory (not shown) in the circuit or the magnetic disk apparatus 109. In other words, the design pattern data is loaded, and an occupancy rate of a graphic to a design pattern in each of grids obtained by virtually dividing an inspection region as grids having a predetermined size as a unit is calculated, and n-bit occupancy rate data is output to the pattern memory (not shown) or the magnetic disk apparatus 109. For example, one grid is preferably set as one pixel. When a resolution of $1/2^8$ ($=1/256$) is given to one pixel, a $1/256$ small region of $1/256$ is allocated to a region of a graphic arranged in a pixel to calculate an occupancy rate in the pixel. The developed image data is stored in the pattern memory or the magnetic disk apparatus 109 as image data in units of areas defined by the 8-bit occupancy data to each pixel.

Data processing (image processing) is performed on the developed image data, and an appropriate filter process is performed on the image data. Optical image data (measurement data) is set in a state in which a filter is activated by a resolution characteristic of the magnifying optical system 104, an aperture effect of the photodiode array 105, or the like, in other words, an analog state in which the data continuously changes. For this reason, a filter process conforming to a predetermined model is also performed on the developed image data which is image data having an image intensity (gray value) on a design side of a digital value so that the developed image data can match with the measurement data. For example, filter processes such as a resizing process which performs a magnifying or reducing process, a corner rounding process, and a blurring process are performed. In this manner, a partial design image corresponding to a partial optical image is formed. The formed partial design image data is sent to the position correcting circuit 140. Like the measurement data, the partial design image data is also, for example, 8-bit signless data for each pixel and expresses brightness gradients of the pixels in numbers 0 to 255. In an alignment step (1) (will be described later), when the developed image is directly used, alignment can be more accurately performed because the image is not blurred. For this reason, the step of the filter process may be omitted.

Figure 6:
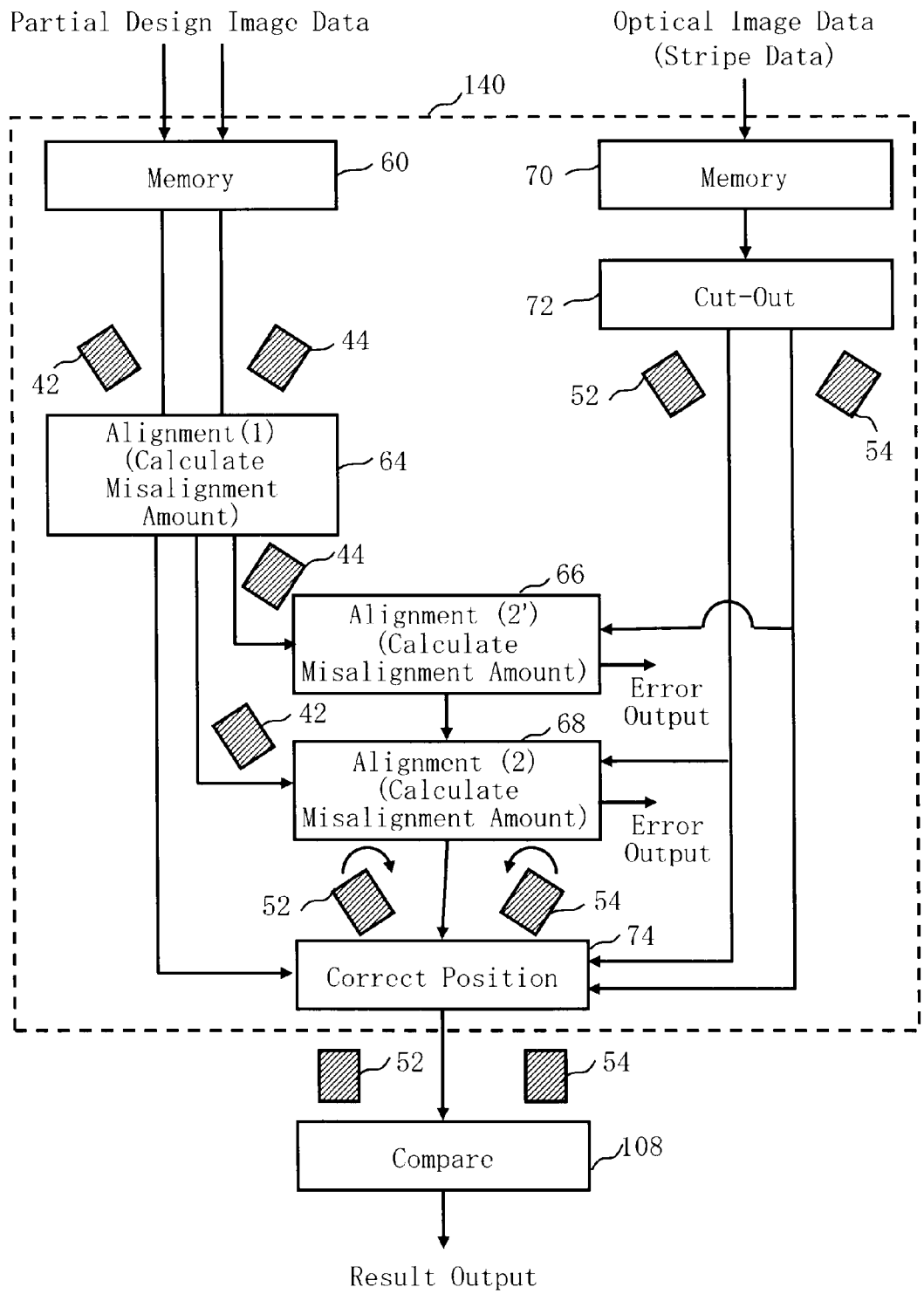
FIG. 6 is a conceptual diagram showing an internal configuration of a position correcting circuit according to Embodiment 1 and a process flow performed from when data is input to the position correcting circuit to when a comparing process is performed.

FIG. 6 is a conceptual diagram showing an internal configuration of the position correcting circuit according to Embodiment 1 and a process flow performed from when data is input to the position correcting circuit to when a comparing process is performed. Every inspection stripe, when the partial design image data corresponding to the partial optical images 52 and 54 of dies to be compared are input to the position correcting circuit 140, the partial design image data are temporarily stored in a memory 60. On the other hand, when optical image data of each of the measured inspection stripes is input to the position correcting circuit 140, the optical image data is temporarily stored in a memory 70.

As a cut-out step, a cut-out unit 72 reads the optical image data from the memory 70 and cuts out the optical image data into a plurality of partial optical image data being images of regions having predetermined sizes. In this case, the partial optical images 52 and 54 which are dies to be compared in the $n^{th}$ inspection stripe are cut out. In this phase, measurement data of the pattern region 10 and measurement data of the pattern region 12 corresponding to the measurement data is cut out.

In this manner, the partial optical images 52 and 54 which are dies to be compared and the partial design images 42 and 44 corresponding to the partial optical images can be prepared as a result. Since the partial optical images 52 and 54 are different from each other in direction and position, the images are consequently determined as a defect when both the partial optical images 52 and 54 are directly compared with each other. In this case, from the design pattern data or the plurality of partial design image data generated from the design pattern data, an amount of distortion of a pattern formed on the photomask 101 can be acquired. Accordingly, as distortion information, a plurality of partial design image data corresponding to a plurality of partial optical image data generated from design pattern data corresponding to an identical pattern formed at plurality of positions with distortion on a target object to be inspected is used to correct positions of the plurality of partial optical image data. In this case, as an example, by using the partial design images 42 and 44 as distortion information, correction of directions and positions of the partial optical images 52 and 54 will be described below.

As the alignment step (1), the alignment process unit 64 performs alignment of the partial design images 42 and 44 to calculate an amount of misalignment. The alignment process unit 64 which is an example of a misalignment amount calculating unit. The alignment process unit 64 performs a parallel moving process in at least one of x and y directions orthogonal to each other to align the partial design images 42 and 44. The alignment process unit 64 performs an image rotating process to align the partial design images 42 and 44. In this case, when the partial design images 42 and 44 are to be aligned, the rotating process is preferably performed in a direction in which arrangement angles of the partial design images 42 and 44 come close to arrangement angles of the partial design images 42 and 44 obtained by cut out while assuming that the plurality of forming positions at which the identical image is formed do not have distortion. In other words, angle correction values to rotate the partial design images 42 and 44 such that pattern sides in the partial design images 42 and 44 are adjusted to the directions of the x axis or the y axis are preferably calculated. In image comparison, more accurate determination can be performed when the pattern sides to be formed are adjusted to the directions of the x axis or the y axis. For this reason, when the directions of the partial optical images 52 and 54 (will be described later) are corrected by using the angle correction values, the pattern sides in the partial optical images 52 and 54 can be adjusted to the directions of the x axis and the y axis. As a result, in the comparing process, an accurate determination can be made. As described above, an amount of misalignment between the partial design images 42 and 44 corresponding to the partial optical images 52 and 54 is calculated.

As an alignment step (2'), an alignment process unit 66 aligns the partial optical image 54 and the partial design image 44 corresponding to the partial optical image 54 to calculate the amount of misalignment. In this case, the alignment process unit 66 performs a parallel moving process in at least one of the x and y directions orthogonal to each other to align the partial optical image 54 and the partial design image 44. The alignment process unit 66 performs an image rotating process to align the partial optical image 54 and the partial design image 44. In this manner, an amount of misalignment between the partial optical image 54 and the partial design image 44 is calculated. When the amount of misalignment is larger than a predetermined threshold, error information is output. In other word, an output unit outputs the error information when an amount of misalignment between each of the plurality of partial optical image data and a respective corresponding partial design image data exceeds a predetermined threshold. When a pattern is accurately formed on the photomask 101, an error between the partial optical image 54 and the partial design image 44 must be originally small. Nevertheless, when the amount of misalignment is excessively large, it is likely that the pattern is not originally formed on the photomask 101 at high accuracy. Alternatively, it is likely that the input design pattern data itself is originally wrong. Therefore, in this case, error information is output to make it possible to cause a user to recognize the circumstances. The error information may be output from the magnetic disk apparatus 109, the magnetic tape apparatus 115, the flexible disk apparatus (FD) 116, the CRT 117, the pattern monitor 118, or the printer 119 which are examples of an output unit.

For alignment between the plurality of regions to be inspected, a relative distance between the regions is aligned by using a specific or arbitrary pattern image being on a target object. However, in Embodiment 1, besides the alignment, an original point of a design image which is distortion information and an original point on the target object may be aligned to align the partial optical image 54 and the partial design image 44 corresponding to the partial optical image 54. For this purpose, as is conventionally performed by an inspection apparatus which performs comparison with a design pattern, alignment may be executed by using a pattern which can specify an original point on a target object.

As the alignment step (2), the alignment process unit 68 performs alignment of the partial optical image 52 and the partial design image 42 corresponding to the partial optical image 52 to calculate an amount of misalignment therebetween. In this case, the alignment process unit 68 performs a parallel moving process in at least one of the x and y directions orthogonal to each other to align the partial optical image 52 and the partial design image 42. The alignment process unit 68 performs an image rotating process to align the partial optical image 52 and the partial design image 42. In this manner, an amount of misalignment between the partial optical image 52 and the partial design image 42 is calculated. When the amount of misalignment is larger than a predetermined threshold, as in the alignment step (2'), error information is output. In this case, when the step of aligning the original point of the design image and an original point on a target object, the alignment step (1), and the alignment step (2') are performed, the images must be aligned without performing the alignment step (2). Therefore, the alignment step (2) may be omitted.

In this case, the order of the alignment step (1), the alignment step (2'), and the alignment step (2) is not limited to the order described above, and may be arbitrarily set. Alternatively, some or all of the steps may be performed in parallel with each other. It is necessary only that the amount of misalignment between the partial design images 42 and 44, the amount of misalignment between the partial optical image 54 and the partial design image 44, and the amount of misalignment between the partial optical image 52 and the partial design image 42 are acquired.

As a position correcting step, the correction unit 74 corrects positions of a plurality of partial optical image data by using the distortion information.

Figure 7A:
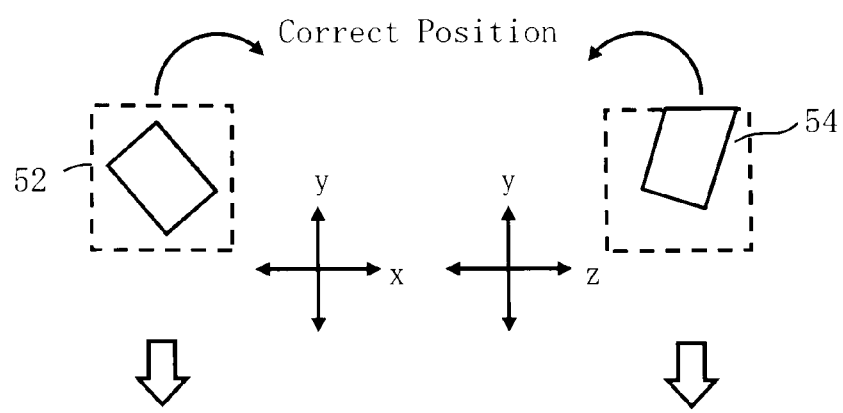
FIGS. 7A and 7B are conceptual diagrams for explaining positional correction of a plurality of partial optical image data according to Embodiment 1.
Figure 7B:
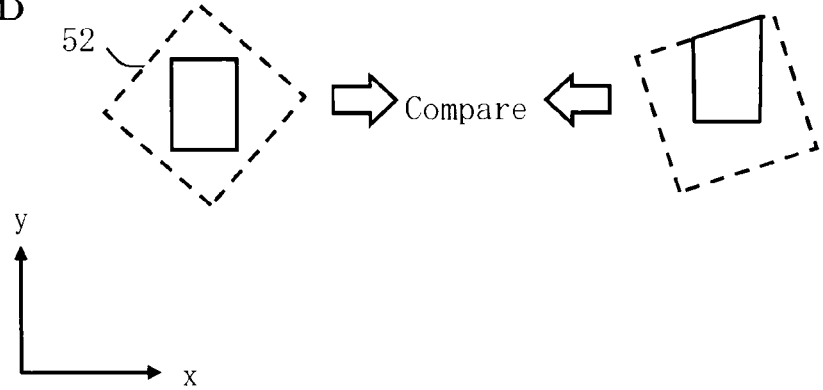

FIGS. 7A and 7B are conceptual diagrams for explaining positional correction of a plurality of partial optical image data according to Embodiment 1. For example, the correction unit 74 relatively corrects an amount of misalignment between the partial design images 42 and 44 with respect to the partial optical images 52 and 54. Then, the amount of misalignment between the partial optical image 54 and the partial design image 44 is corrected with respect to the partial optical image 54. The amount of misalignment between the partial optical image 52 and the partial design image 42 is corrected with respect to the partial optical image 52. In this manner, the positions of the partial optical images 52 and 54 can be corrected. As shown in FIG. 7A, the correction unit 74, performs a parallel moving process in at least one of the x and y directions orthogonal to each other to correct the positions of the partial optical images 52 and 54. The correction unit 74 performs an image rotating process to correct the positions of the partial optical images 52 and 54 as shown in FIG. 7B.

Figure 8:
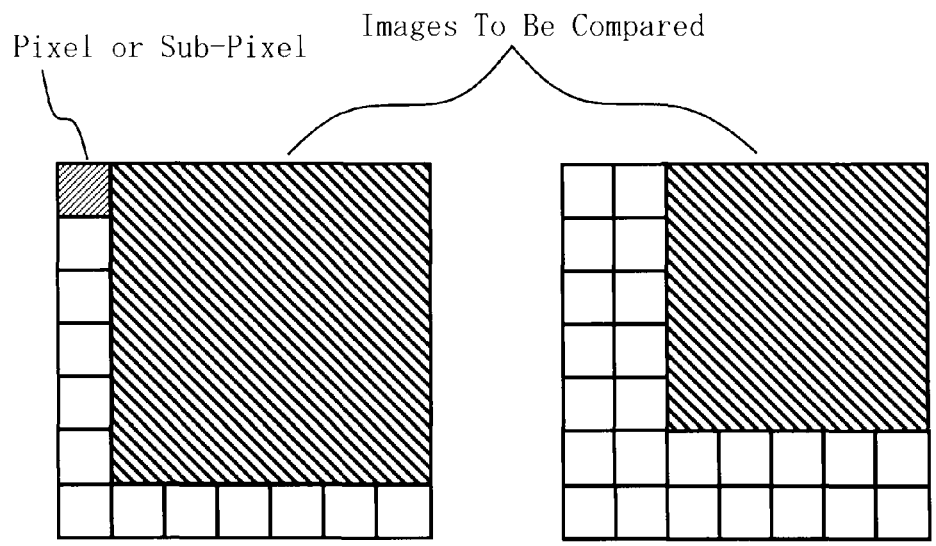
FIG. 8 is a conceptual diagram for explaining an example of a parallel moving process according to Embodiment 1.

FIG. 8 is a conceptual diagram for explaining an example of a parallel moving process according to Embodiment 1. When the partial optical images 52 and 54 which are images to be compared with each other are misaligned on a pixel to pixel basis or sub-pixels, the parallel moving process is performed in at least one of the x and y directions. For example, as in the example shown in FIG. 8, when the partial optical images are misaligned by 1 pixel (or 1 sub-pixel) in the x or y direction, a parallel moving process of 1 pixel (or 1 sub-pixel) is performed in the x or y direction to correct the positions of the partial optical images 52 and 54.

Figure 9:
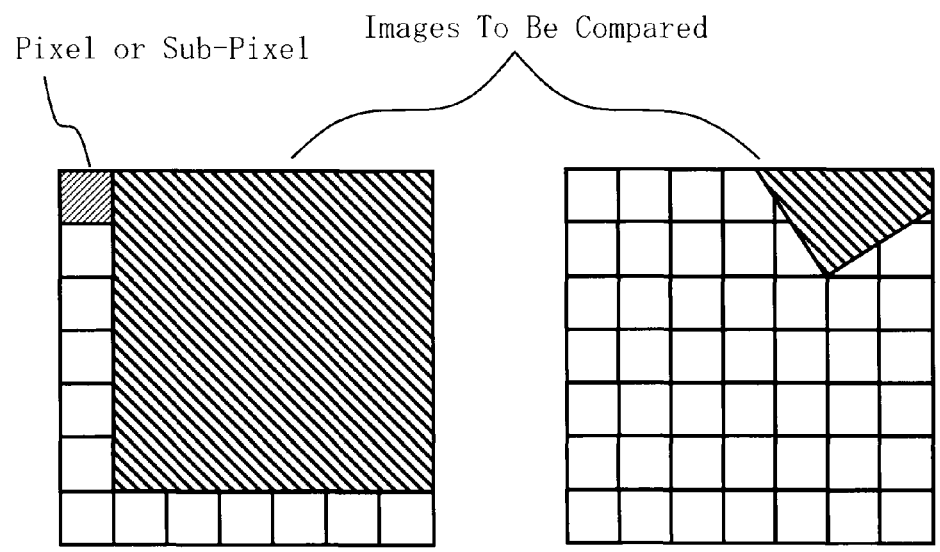
FIG. 9 is a conceptual diagram for explaining an example of a rotating process according to Embodiment 1.

FIG. 9 is a conceptual diagram for explaining an example of a rotating process according to Embodiment 1. When the partial optical images 52 and 54 which are images to be compared with each other cannot be aligned by the parallel moving process as in the example in FIG. 9, the rotating process may be performed.

The correction unit 74 preferably performs the image rotating process in a direction in which the arrangement angles of the partial optical images are close to the arrangement angles of the partial optical images obtained by cut out when each of a plurality of identical patterns is respectively formed at the corresponding position of the plurality of forming positions with no distortion. In other word, The correction unit 74 preferably performs the rotating process in a direction in which the arrangement angles of the partial optical images are close to the arrangement angles of the partial optical images obtained by cut out while assuming that the plurality of forming positions at which the partial optical images 52 and 54 are formed do not have distortion. When the amount of misalignment between the partial design images 42 and 44 is to be acquired, a rotating process may be performed by an amount of angle correction to rotate the images such that pattern sides of the obtained partial design images 42 and 44 are adjusted to the direction of the x axis or the y axis. With this rotating process, as shown in FIG. 7(*b*), pattern sides in the partial optical images 52 and 54 can be adjusted to the direction of the x axis or the y axis. The data of the partial optical images 52 and 54 the positions of which are corrected as described above are output to the comparison circuit 108.

With the above comparison, even in the die-die inspection for the target objects to be inspected on which patterns distorted in advance are formed, pattern positions in the partial optical images which are dies to be compared can be aligned.

As a comparing step, the comparison circuit 108 compares a plurality of corrected partial optical image data of both the corresponding dies against each other on a pixel to pixel basis under a predetermined determination condition. The comparison circuit 108 is an example of the comparison unit. The aligned partial optical images 52 and 54 are compared on a pixel to pixel basis according to the predetermined determination condition to determine the presence/absence of a defect. For example, the determination condition corresponds to a threshold used when both the images are compared with each other on a pixel to pixel basis according to a predetermined algorithm to determine the presence/absence of a defect. Alternatively, for example, the determination condition corresponds to a comparison algorithm used when both the images are compared with each other to determine the presence/absence of a defect. A comparison result is output. The comparison result may be output from the magnetic disk apparatus 109, the magnetic tape apparatus 115, the flexible disk apparatus (FD) 116, the CRT 117, the pattern monitor 118, or the printer 119.

As described above, in Embodiment 1, by using the design pattern data or the partial design image data generated from the design pattern data as distortion information, the directions and the positions of the partial optical images 52 and 54 are corrected to perform accurate inspection in the die-die inspection for the target objects to be inspected on which the patterns distorted in advance are formed.

Embodiment 2

In Embodiment 1, the method of inputting a pattern in designing a mask as distortion information. However, in execution of the die-die inspection, a case in which a design pattern cannot be acquired may occur. In preparation for the cases, in Embodiment 2, a configuration which uses exposure apparatus information indicating an amount of misalignment of patterns generated when the patterns are transferred by an exposure apparatus which uses a target object to be inspected as an exposure mask will be described below. In Embodiment 1, when a mask pattern is distorted to obtain an expected shape on a wafer. By viewing this from the other side, if an amount of distortion when a pattern is transferred by the exposure apparatus using the photomask 101 is known, an amount of misalignment (misalignment amount) of the pattern can also be calculated.

Figure 10:
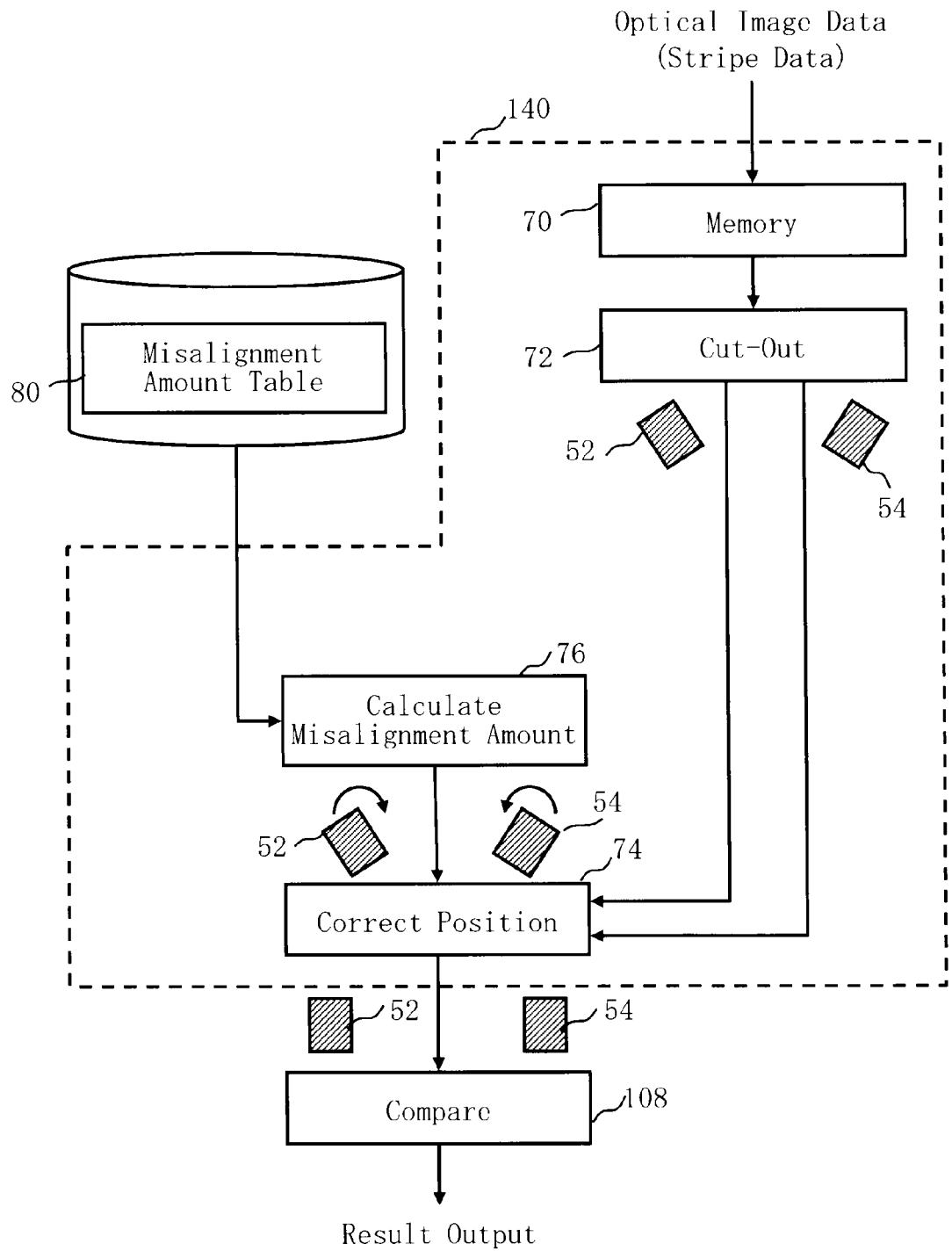
FIG. 10 is a conceptual diagram showing an internal configuration of a position correcting circuit according to Embodiment 2 and a process flow performed from when data is input to the position correcting circuit to when a comparing process is performed.

FIG. 10 is a conceptual diagram showing an internal configuration of a position correcting circuit according to Embodiment 2 and a process flow performed from when data is input to the position correcting circuit to when a comparing process is performed. The internal configuration of the position correcting circuit is the same as the internal configuration of the position correcting circuit in FIG. 6 except that a misalignment amount calculating unit 76 is provided in place of the memory 60 and the alignment process units 64, 66, and 68. The other apparatus configuration is the same as that in FIG. 1. The contents which will not be especially explained below are the same as those in Embodiment 1. In the magnetic disk apparatus 109, exposure apparatus information is input from the outside and stored.

Figure 11:
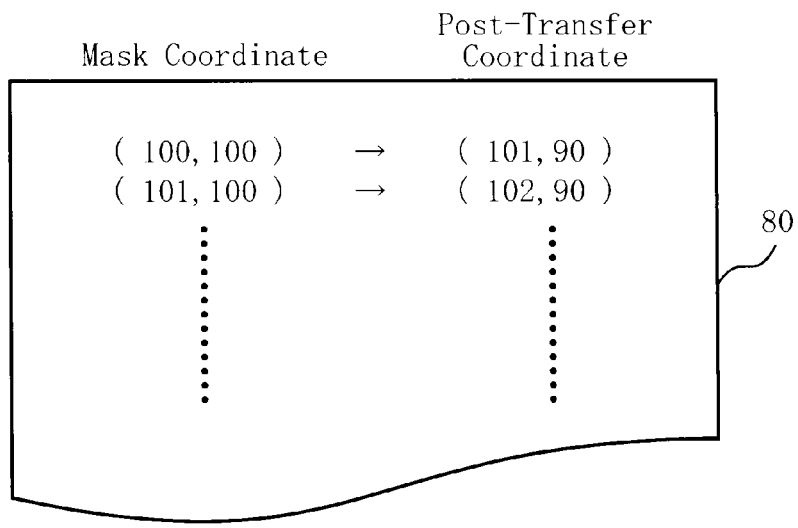
FIG. 11 is a conceptual diagram showing an example of exposure apparatus information according to Embodiment 2.

FIG. 11 is a conceptual diagram showing an example of exposure apparatus information according to Embodiment 2. In FIG. 11, in a misalignment amount table 80 which is an example of the exposure apparatus information, mask coordinates and post-transfer coordinates at which the mask coordinates are located after the transfer is performed by the exposure apparatus are defined. For example, it is understood that, if a position of coordinates (100,100) is changed to a position of coordinates (101,90) after the transfer, a pattern at the position of the coordinates (101, 90) on the photomask 101 when the pattern is not distorted is changed to the position of the coordinates (100,100) on the photomask 101 inspected in Embodiments 1 and 2.

Figure 12A:
FIGS. 12A and 12B are conceptual diagrams for explaining positional correction of a plurality of partial optical image data according to Embodiment 2.
Figure 12B:

FIGS. 12A and 12B are conceptual diagrams for explaining positional correction of a plurality of partial optical image data according to Embodiment 2.

Figure 13:
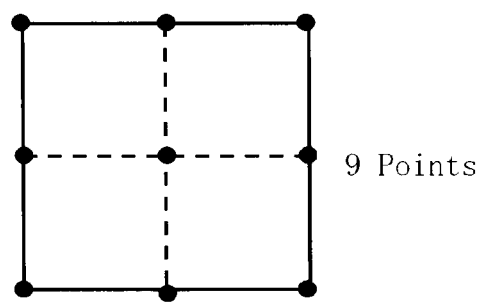
FIG. 13 is a diagram showing an example of typical points to which positional correction for a plurality of partial optical image data is performed according to Embodiment 2.

FIG. 13 is a diagram showing an example of typical points to which positional correction for a plurality of partial optical image data is performed according to Embodiment 2.

As a misalignment amount calculating step, the misalignment amount calculating unit 76 inputs the cut-out partial optical images 52 and 54. Then, the misalignment amount calculating unit 76 reads the misalignment amount table 80 from the magnetic disk apparatus 109 to calculate an amount of misalignment between the partial optical images 52 and 54. The misalignment amount calculating unit 76 calculates an amount of misalignment to correct coordinates after the transfer with reference to the misalignment amount table 80 with respect to coordinates of pixels at a plurality of typical points of the partial optical images 52 and 54. For example, as shown in FIG. 12A, when the partial optical images 52 and 54 have distorted positions and directions, as shown in FIG. 13, a total of 9 points including the 4 corners of the partial optical images and an intermediate point therebetween are regarded as the typical points. With respect to the misalignment amount table 80 for the coordinates of the pixels of the 9 typical points of the partial optical images 52 and 54, amounts of misalignment to correct the coordinates after the transfer are calculated. In this case, although the 9 typical points are used, the number of typical points is not limited to 9, but may be arbitrarily set. For example, the number of typical points may be two or four.

As a position correcting step, the correction unit 74 corrects positions of a plurality of partial optical image data by using the exposure apparatus information as distortion information. The correction unit 74 corrects the calculated amounts of misalignment to the corresponding partial optical images 52 and 54. The correction unit 74 performs a parallel moving process in at least one of the x and y directions orthogonal to each other along the calculated amounts of misalignment to correct the positions of the partial optical images 52 and 54. The correction unit 74 performs an image rotating process to correct the positions of the partial optical images 52 and 54. With the correction, as shown in FIG. 12B, the partial optical images 52 and 54 at the post-transfer coordinate positions can be obtained. In general, in the partial optical images 52 and 54 at the post-transfer coordinate positions, the pattern sides in the partial optical images 52 and 54 are frequently designed to be adjusted to the direction of the x axis or the y axis. Therefore, by the positional correction, the pattern sides in the partial optical images 52 and 54 can be adjusted to the direction of the x axis or the y axis. As a result, in a comparing process, an accurate determination can be made.

In this case, an inputting method of data of the exposure apparatus information may be a method of inputting information such as individual parameters of the exposure apparatus or optical conditions of the exposure apparatus, or may be realized by inputting data of an amount of distortion itself additionally calculated from the pieces of information. The distortion information may be managed with coordinates or with the number of pixels, for example, counted from the beginning of an inspection stripe or the like. As units in which the distortion information is stored, inspection stripe units are advantageous to execute the inspection.

With the above correction, even in the die-die inspection performed on the target objects to be inspected on which patterns distorted in advance are formed, pattern positions in the partial optical images which are dies to be compared can be aligned.

As a comparing step, the comparison circuit 108 compares a plurality of corrected partial optical image data of both the corresponding dies on a pixel to pixel basis under a predetermined determination condition. The processing contents are the same as those in Embodiment 1.

As described above, in Embodiment 2, when the directions and positions of the partial optical images 52 and 54 are corrected by using the exposure apparatus information as distortion information, accurate inspection can be performed in the die-die inspection for target objects to be inspected on which patterns distorted in advance are formed.

Figure 14:
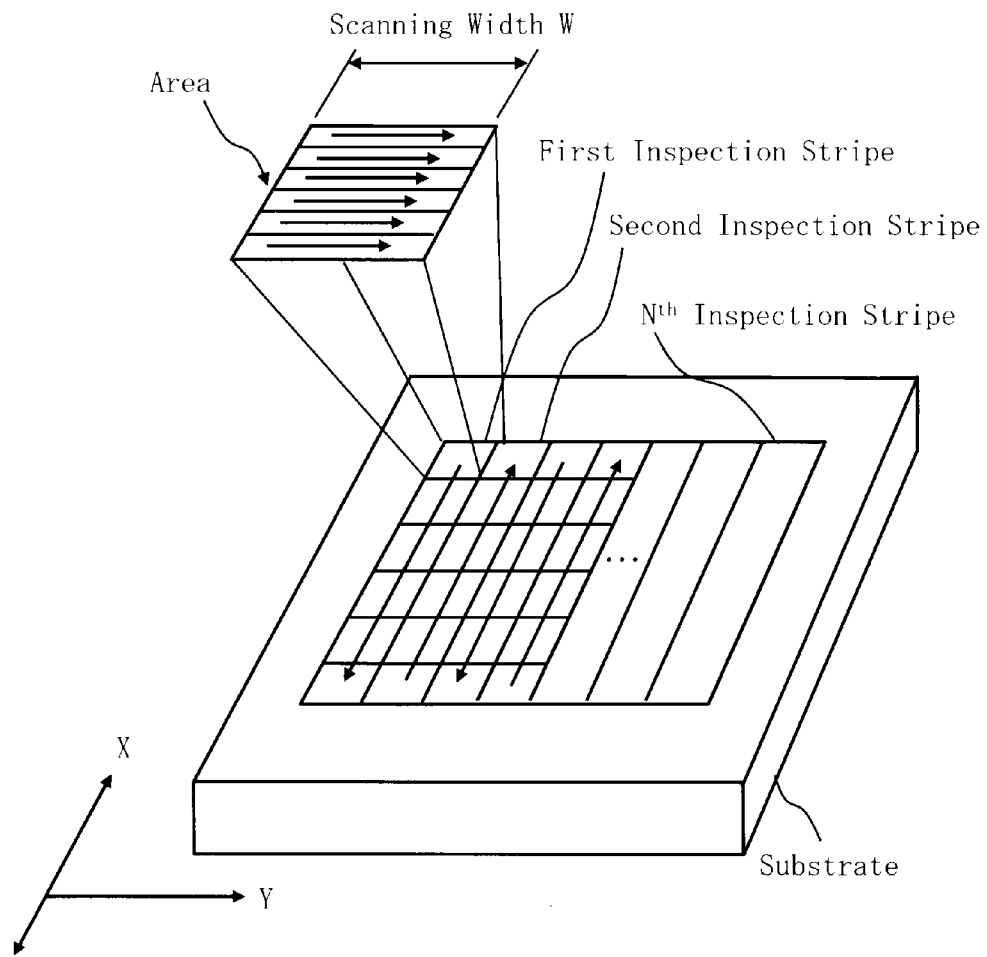
FIG. 14 is a diagram for explaining another optical image acquiring method.

FIG. 14 is a diagram for explaining another optical image acquiring method. In the configuration in FIG. 1 or the like, the photodiode array 105 which causes light to be simultaneously incident on pixels the number of which corresponds the scanning width W is used. However, the configuration is not limited to the method, and as shown in FIG. 14, a method which causes a laser scanning optical apparatus (not shown) to scan with a laser beam in the Y direction while sending the XYθ table 102 in the X direction at a constant speed each time movement at a constant pitch is detected by a laser interferometer to detect a transmitted light or a reflected light to acquire a two-dimensional image for each area having a predetermined size may be used.

The "units", the "circuits", or the "steps" described in the above explanation can be configured by programs which are operable by a computer. Alternatively, the units, the circuits, and the steps may be executed by not only programs which are software but also combinations of hardware and software. Furthermore, the units, the circuits, or the steps may be executed by combinations of hardware and firmware. When the units, the circuits, or the steps are configured by programs, the programs are recorded on a recording medium such as the magnetic disk apparatus 109, the magnetic tape apparatus 115, the FD 116, or a ROM (Read Only Memory). For example, the position circuit 107, the comparison circuit 108, the design image forming circuit 112, the autoloader control circuit 113, the table control circuit 114, the position correcting circuit 140, and the like which constitute an arithmetic control unit may be configured by electric circuits or may be realized as software which can be processed by the control computer 110. The circuits may be realized by combinations of electric circuits and software.

The embodiments have been described with reference to the concrete examples. However, the present invention is not limited to the concrete examples. For example, in the embodiments, although a transmission optical system is used by using a transmitted light, a configuration which uses the reflected light, or which simultaneously uses the transmitted light and the reflected light may be used.

Parts such as an apparatus configuration, a control method which are not directly necessary for the explanation of the present invention are omitted. However, a necessary apparatus configuration or control method can be arbitrarily used.

In addition, all pattern inspection method or all pattern inspection apparatuses which include the elements of the present invention and can be arbitrarily changed in design by those skilled in the art are included in the spirit and scope of the invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection apparatus comprising:
an optical image acquiring unit, with a computer or an electric circuit, configured to acquire optical image data of a target object on which each of a plurality of identical patterns is respectively formed at a respective corresponding position of a plurality of forming positions with distortion;
a cut-out unit, with the computer or an electric circuit, configured to cut out a plurality of partial optical image data from the optical image data;
a correction unit, with the computer or an electric circuit, configured to correct positions of the plurality of partial optical image data by using distortion information from which each amount of distortion of the plurality of identical patterns respectively formed at the respective corresponding position of the plurality of forming positions on the target object can be acquired; and
a comparison unit, with the computer or an electric circuit, configured to compare a plurality of corrected partial optical image data against each other on a pixel to pixel basis,
wherein each of a plurality of partial design image data corresponding to the plurality of partial optical image data is respectively formed with distortion,
the correction unit performs alignment of the plurality of partial design image data to calculate a first amount of misalignment, aligns one of the plurality of partial optical image data and one of the plurality of partial design image data corresponding to the one of the plurality of partial optical image data to calculate a second amount of misalignment, aligns another one of the plurality of partial optical image data and another one of the plurality of partial design image data corresponding to the another one of the plurality of partial optical image data to calculate a third amount of misalignment, and corrects positions of the plurality of partial optical image data by using the first, second, and third amount of misalignment as the distortion information.

2. The apparatus according to claim 1, wherein a plurality of partial design image data corresponding to the plurality of partial optical image data, the plurality of partial design image data being generated based on design pattern data corresponding to the plurality of identical patterns formed at the plurality of forming positions on the target object with distortion, is used as the distortion information.

3. The apparatus according to claim 2, further comprising an output unit, with the computer or an electric circuit, configured to output error information when an amount of misalignment between each of the plurality of partial optical image data and a respective corresponding partial design image data exceeds a predetermined threshold.

4. The apparatus according to claim 1, wherein exposure apparatus information indicating amounts of misalignment of patterns generated when the patterns are transferred by an exposure apparatus using the target object as an exposure masks, is used as the distortion information.

5. The apparatus according to claim 1, wherein the correction unit performs a parallel moving process in at least one of x and y directions orthogonal to each other to correct the positions of the plurality of partial optical image data.

6. The apparatus according to claim 1, wherein the correction unit corrects the positions of the plurality of partial optical image data by performing an image rotating process.

7. The apparatus according to claim 6, wherein the correction unit performs the image rotating process in a direction in which arrangement angles of the plurality of partial optical image data come close to arrangement angles of a plurality of partial optical image data obtained by cut out when each of a plurality of identical patterns is respectively formed at the corresponding position of the plurality of forming positions with no distortion.

8. A pattern inspection method comprising:
acquiring optical image data of a target object on which each of a plurality of identical patterns is formed at a respective corresponding position of a plurality of forming positions with distortion;
cutting out a plurality of partial optical image data from the optical image data;
correcting positions of the plurality of partial optical image data by using distortion information from which each amount of distortion of the plurality of identical patterns respectively formed at the respective corresponding position of the plurality of forming positions on the target object can be acquired; and
comparing a plurality of corrected partial optical image data against each other on a pixel to pixel basis, to output a result of the comparing,
wherein each of a plurality of partial design image data corresponding to the plurality of partial optical image data is respectively formed with distortion,
alignment of the plurality of partial design image data is performed to calculate a first amount of misalignment, one of the plurality of partial optical image data and one of the plurality of partial design image data corresponding to the one of the plurality of partial optical image data are aligned to calculate a second amount of misalignment, another one of the plurality of partial optical image data and another one of the plurality of partial design image data corresponding to the another one of the plurality of partial optical image data are aligned to calculate a third amount of misalignment, and positions of theplurality of partial optical image data are corrected by using the first, second, and third amount of misalignment as the distortion information.

9. The method according to claim 8, wherein a plurality of partial design image data corresponding to the plurality of partial optical image data, the plurality of partial design image data being generated based on design pattern data corresponding to the plurality of identical patterns formed at the plurality of forming positions on the target object with distortion, is used as the distortion information.

10. The method according to claim 8, wherein exposure apparatus information indicating amounts of misalignment of patterns generated when the patterns are transferred by an exposure apparatus using the target object as an exposure masks, is used as distortion information.

* * * * *